US011774460B2

(12) United States Patent
Roy (10) Patent No.: US 11,774,460 B2
(45) Date of Patent: Oct. 3, 2023

(54) DIAGNOSTIC OR PREDICTOR OF RELAPSING REMITTING MULTIPLE SCLEROSIS

(71) Applicant: Dignity Health, San Francisco, CA (US)

(72) Inventor: Dolly Roy, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 112 days.

(21) Appl. No.: 16/311,097

(22) PCT Filed: Jun. 30, 2017

(86) PCT No.: PCT/US2017/040445
§ 371 (c)(1),
(2) Date: Dec. 18, 2018

(87) PCT Pub. No.: WO2018/006051
PCT Pub. Date: Jan. 4, 2018

(65) Prior Publication Data
US 2020/0309792 A1 Oct. 1, 2020

Related U.S. Application Data

(60) Provisional application No. 62/357,787, filed on Jul. 1, 2016.

(51) Int. Cl.
*G01N 33/68* (2006.01)
*A61P 25/00* (2006.01)
*A61K 31/573* (2006.01)
*A61K 31/727* (2006.01)
*G01N 33/86* (2006.01)

(52) U.S. Cl.
CPC ....... *G01N 33/6896* (2013.01); *A61K 31/573* (2013.01); *A61K 31/727* (2013.01); *A61P 25/00* (2018.01); *G01N 33/86* (2013.01); *G01N 2333/755* (2013.01); *G01N 2800/285* (2013.01); *G01N 2800/54* (2013.01)

(58) Field of Classification Search
CPC ..... G01N 33/6896; G01N 33/86; A61P 25/00; A61K 31/573; A61K 31/727
See application file for complete search history.

(56) References Cited

U.S. PATENT DOCUMENTS

| 2003/0211460 | A1 | 11/2003 | Nelsestuen | |
|---|---|---|---|---|
| 2010/0062471 | A1 | 3/2010 | Kantor et al. | |
| 2010/0081160 | A1 | 4/2010 | Dotan et al. | |
| 2012/0071339 | A1* | 3/2012 | Bahn | G01N 33/564 |
| | | | | 506/9 |
| 2014/0308680 | A1 | 10/2014 | Van Lieshout | |
| 2015/0031562 | A1 | 1/2015 | Kantor et al. | |
| 2015/0037327 | A1 | 2/2015 | Keller et al. | |

FOREIGN PATENT DOCUMENTS

| WO | 2002060471 | A2 | 8/2002 | |
|---|---|---|---|---|
| WO | 2010136232 | A1 | 12/2010 | |
| WO | 2014018932 | A1 | 1/2014 | |
| WO | 2015063604 | A2 | 5/2015 | |
| WO | WO-2015063604 | A2 * | 5/2015 | ........... C12Q 1/6883 |

OTHER PUBLICATIONS

Hill-Eubanks et al. "von Willebrand factor is a cofactor for thrombin-catalyzed cleavage of the factor VIII light chain", J Biol Chem. Oct. 15, 1990;265(29):17854-8. (Year: 1990).*
Han et al. "Proteomic analysis of active multiple sclerosis lesions reveals therapeutic targets", Nature. Feb. 28, 2008;451(7182):1076-81 (Year: 2008).*
Bruzelius, Maria, "Exploration of Novel Mechanisms and Biomarkers for Venous Thromboembolism: A Genetics and Proteomics Study", PQDT—Global ProQuest Dissertations Publishing. (2015). (Year: 2015).*
Peeters et al. "The risk of venous thromboembolism in patients with multiple sclerosis: the Clinical Practice Research Datalink", J Thromb Haemost. Apr. 2014;12(4):444-51. (Year: 2012).*
Verbot, Norah G et al. "Thrombin mutant W215A/E217A treatment improves neurological outcome and attenuates central nervous system damage in experimental autoimmune encephalomyelitis." Metabolic brain disease vol. 30,1 (2014): 57-65.
Waldman A. M.D. et al. Multiple Sclerosis in Children: An update on Clinical Diagnosis, Theraputic, Strategies and Research; Lancet Neurol; Sep. 2014; 13(9): 936-948.
Robinson, Derrick M.D. et al. Disease Modifying Therapies in Multiple Sclerosis; Overview and Treatment Consideration Federal Practicioner: 2016; p. 28-34.
Llana, K. Sand. Classification Diagnoses, and Differential Diagnosis of Multiple Sclerosis: www.co-neurolgy.com vol. 28 No. 3: Jun. 2015.

(Continued)

*Primary Examiner* — Amy E Juedes
*Assistant Examiner* — Peter Johansen
(74) *Attorney, Agent, or Firm* — Polsinelli PC (57) ABSTRACT

Provided herein is a method of detecting or predicting a relapse of multiple sclerosis in an individual afflicted with a form of multiple sclerosis, comprising: (a) providing a blood sample of the individual; (b) testing the blood sample to determine a protein activity or protein level, wherein the protein is Factor VIII, von Willebrand factor, or Protein C; and (c) detecting or predicting a relapse of multiple sclerosis in the individual if the protein activity or protein level is elevated compared to the protein activity or protein level in an individual not afflicted with the form of multiple sclerosis and patients' own baseline values. Also provided herein is a method of treating an individual afflicted with multiple sclerosis, who is experiencing a relapse or predicted to experience a relapse, comprising treating the individual by administering a dose of a steroid or anti-coagulation compound effective to alleviate the symptom of multiple sclerosis.

12 Claims, 10 Drawing Sheets

(56) References Cited

OTHER PUBLICATIONS

Thomas, Lisa., et al. Is Multiple Sclerosis a Risk for Hypercoagulation States or Breast Cancer? A Case Report and a Literature Review to Assess Options. Blood 2011; 118:4665.
Rajpal et al., "Elevated Von Willebrand Factor Antigen Levels are an Independent Risk Factor for Venous Thromboembolism: First Report from North India", Indian J Hematol Blood Transfus, 2019, vol. 35, Issue 3, pp. 489-495.
European Patent Office, Communication Pursuant to Article 94(3) EPC, Application No. 17821415.1, dated Nov. 2, 2022, 9 pages.
Cpipih, N N et al. "Faktop foh Villebpahda i molekyly adGezii y patsiehtoB c pacceyahhym cklepozom von Willebrand factor and adhesion molecules in patients with multiple sclerosis", XP055619447, Retrieved from the Internet URL: https://pdfs.semanticscholar.org/593f/ea70fe1da1b89d38f1780f89d0f16dafdf1d.pdf, Jan. 1, 2014.
Kohriyama, T. et al., "Endothelial cell activation and/or injury in multiple sclerosis: analysis with von Willebrand factor and thrombomodulin," U.S. National Library of Medicine (NLM), vol. 37, No. 4, Apr. 1997, pp. 287-291.
Office Action issued in Chinese Application No. 201780040017.1 dated Oct. 15, 2021, 10 pages.
Berkovich et al., Treatment of Acute Relapses in Multiple Sclerosis, Neurotherapeutics, vol. 10, pp. 97-105, Dec. 11, 2012.
Balkuv et al., The effects of thrombomodulin and activated protein C on the pathogenesis of multiple sclerosis, Mult Scler Relat Disord., vol. 8, pp. 131-135, May 17, 2016.
Ingram et al., Systemic complement profiling in multiple sclerosis as a biomarker of disease state, Mult Scler., vol. 18, No. 10, pp. 1401-1411, Feb. 21, 2012.
Hill-Eubanks et al., von Willebrand factor is a cofactor for thrombin-catalyzed cleavage of the factor VIII light chain, J Biol Chem., vol. 265, No. 29, pp. 17854-17858, Jan. 15, 1990.
International Search Report and Written Opinion issued in PCT/US2017/040445 dated Sep. 18, 2017, 11 pages.
Examination Report issued in Australian Application No. 2017286979, Jul. 6, 2022, 5 pages.
Office Action issued in Chinese Application No. 201780040017.1 dated Mar. 23, 2022, 9 pages.
European Patent Office, Communication Pursuant to Article 94(3) EPC, Application No. 17821415.1, dated Apr. 6, 2023, 4 pages.
Israel Patent Office, Substantive Examination Report, Application No. 264044, dated Aug. 2, 2023, 11 pages.

* cited by examiner

DIAGNOSTIC OR PREDICTOR OF RELAPSING REMITTING MULTIPLE SCLEROSIS

CROSS REFERENCE TO RELATED APPLICATIONS

This application is a National Phase of International Application No. PCT/US2017/040445, filed Jun. 30, 2017, which designated the U.S., and that International Application was published under PCT Article 21(2) in English. This application also includes a claim of priority under 35 U.S.C. § 119(e) to U.S. Provisional Application No. 62/357,787, filed Jul. 1, 2016, the entirety of which is hereby incorporated by reference.

FIELD OF THE INVENTION

The present disclosure is in the medical and pharmacological field, specifically in the field of multiple sclerosis.

BACKGROUND OF THE DISCLOSURE

Multiple Sclerosis or MS is an autoimmune disease affecting the central nervous system. Multiple sclerosis is a disease of unknown etiology with a prolonged course involving many remissions and relapses. Some people may live with multiple sclerosis for years without suffering serious symptoms. Others may rapidly become disabled. It is unclear why the course of the disease varies so widely. However, most people with multiple sclerosis experience periodic relapses, also called flare-ups, exacerbations, or attacks. These can be mild or severe. Symptoms can include muscle weakness, visual disturbances, balance problems, memory loss, and/or loss of bowel or bladder control.

Today, drugs used for multiple sclerosis drug therapy can be divided into two groups: drugs for symptomatic treatments, and drugs modifying the course of multiple sclerosis. Drugs used for symptomatic treatment of multiple sclerosis include steroids, such as, glucocorticoids.

However, at present there are no known methods for predicting or diagnosing if a patient suffering from multiple sclerosis is about to experience a relapse. If patients did suffer a relapse, there are no known methods for predicting or diagnosing the probability for recovering from the relapse with standard symptomatic treatments. Such a prediction or diagnosis would help the patient and the doctor to monitor the progress of the relapse, and prevent the relapse from being a severe relapse.

SUMMARY OF THE DISCLOSURE

Various embodiments include a method of diagnosing susceptibility for a relapse for acute severe multiple sclerosis (MS) in an individual, comprising obtaining a sample from the individual, assaying the sample to determine the presence or absence of an elevated level of one or more biomarkers associated with acute severe MS relative to a healthy subject and/or the baseline of the individual, and diagnosing susceptibility for a relapse for acute severe MS in the individual based on the presence of one or more biomarkers. In another embodiment, the one or more biomarkers comprise an elevated Factor VIII clotting activity. In another embodiment, the one or more biomarkers comprise elevated von Willebrand Factor (VWF) antigen levels. In another embodiment, the presence of one or more biomarkers are associated with an increase in risk of disability progression. In another embodiment, the multiple sclerosis in the individual is in remission.

Other embodiments include a method of determining a risk of relapse of multiple sclerosis (MS) in an individual afflicted with a form of multiple sclerosis, comprising obtaining a blood sample of the individual, testing the blood sample to determine a protein activity and/or level, wherein the protein is Factor VIII, von Willebrand factor, or Protein C; and determining a risk of relapse of MS in the individual if the protein activity and/or level is elevated relative to a subject not afflicted with the form of MS and/or the baseline of the individual. In another embodiment, the form of MS is relapsing-remitting MS. In another embodiment, the multiple sclerosis in the individual is in remission. In another embodiment, the blood sample test to determine the protein activity or protein level is performed simultaneously with other blood tests, such as, partial thromboplastin time (PTT) test, International Normalized Ratio (INR) test, and erythrocyte sedimentation rate (ESR) test. In another embodiment, the blood sample tests are performed at least once per month during the treatment period and/or monitoring period of MS. In another embodiment, an elevated Factor VIII activity indicates increased weakness and/or sensory impairment. In another embodiment, the individual has an elevated Factor VIII activity or level when the Factor VIII level is equal to, or more than, 160. In another embodiment, the individual has an elevated Factor VIII activity or level when the Factor VIII level is more than 191. In another embodiment, the individual has an elevated Factor VIII activity or level when the Factor VIII level is more than 200. In another embodiment, the individual has an elevated von Willebrand Factor activity when the von Willebrand Factor activity is more than 215. In another embodiment, the individual has an elevated von Willebrand Factor level when the von Willebrand Factor level is more than 214. In another embodiment, the method is used for patients who are at risk for more severe relapses. In another embodiment, the method is used for patients who are at risk of disability resulting from the relapse of MS.

Other embodiments include a method of treating an individual, comprising detecting and/or predicting a relapse of multiple sclerosis (MS) in the individual, and treating the individual by administering a therapeutically effective dosage of a steroid and/or anti-coagulation compound effective to alleviate MS symptoms. In another embodiment, detecting and/or predicting a relapse of MS comprises determining the presence of an elevated level of one or more biomarkers associated with acute severe MS relative to a healthy subject. In another embodiment, the method further comprises administering a disease-modifying therapy and/or agent. In another embodiment, the anti-coagulation compound is Enoxaparin (LOVENOX), Rivaroxaban (XARELTO), Dabigatran (PRADAXA), or Apixaban (ELIQUIS). In another embodiment, the steroid is a corticosteroid. In another embodiment, the steroid is dexamethasone, prednisone, methyl-prednisolone, or corticotropin (ACTHAR). In another embodiment, the anti-coagulation compound is Xarelto. In another embodiment, the anti-coagulation compound is a heparin derivative. In another embodiment, the anti-coagulation compound is Lovenox, Enoxaperin, or heparin. In another embodiment, the method comprises administering solumedrol.

Various embodiments include a method for an in-home and/or an in-hospital diagnosis of a relapse of multiple sclerosis (MS) in an individual, afflicted with a form of MS, comprising providing an in-home and/or an in-hospital testing kit for Factor VIII protein activity or level, providing a blood sample of the patient, testing the Factor VIII protein activity or level in the blood sample of the individual by using the in-home and/or an in-hospital testing kit, and diagnosing a relapse of multiple sclerosis in the individual based on the elevated level or activity of Factor VIII protein compared to the activity or level of Factor VIII protein in an individual not afflicted with the form of multiple sclerosis and/or twice the value of a baseline of the individual. In another embodiment, the form of MS is relapsing-remitting multiple sclerosis. In another embodiment, the need for evaluation by a physician is determined based on the blood sample test result. In another embodiment, the need for evaluation by a physician is determined if the level or activity of Factor VIII protein is more than 160. In another embodiment, the recovery from a relapse of multiple sclerosis is determined based on the blood sample test result.

Other features and advantages of the invention will become apparent from the following detailed description, taken in conjunction with the accompanying drawings, which illustrate, by way of example, various embodiments of the invention.

DETAILED DESCRIPTION

Figure 1:
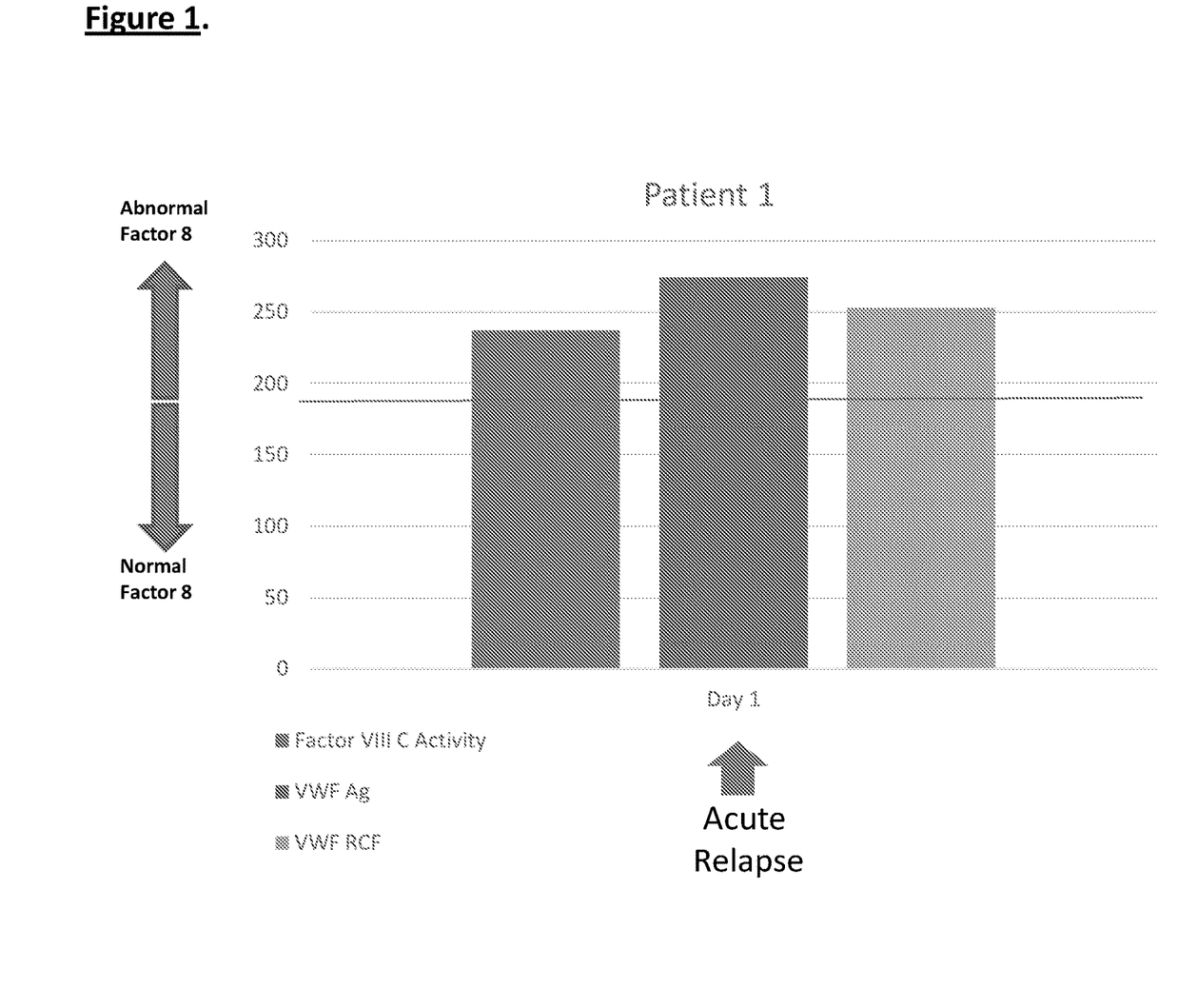
FIG. 1 depicts, in accordance with embodiments herein, acute multiple sclerosis (MS) relapse with slurred speech and arm weakness. The subject is aged in her 70s and is a woman with established MS diagnosis and on no disease-modifying therapy.
Figure 2:
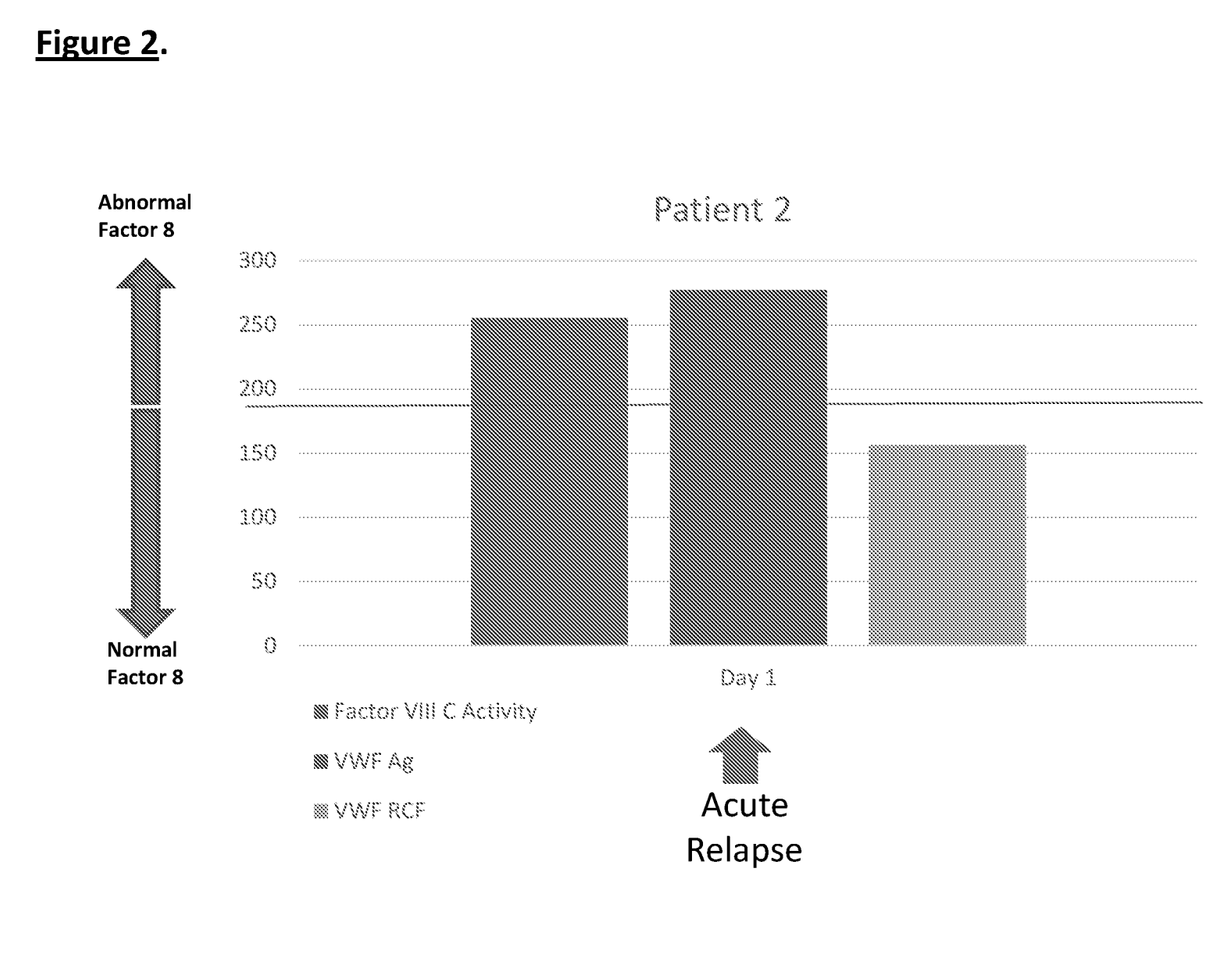
FIG. 2 depicts, in accordance with embodiments herein, acute relapse with resistant gait ataxia and facial numbness with new enhancing brainstem lesion. The subject is aged in her 50s and is a woman with established diagnosis of MS, and on no disease-modifying therapy, after receiving standard solumedrol treatment.
Figure 3:
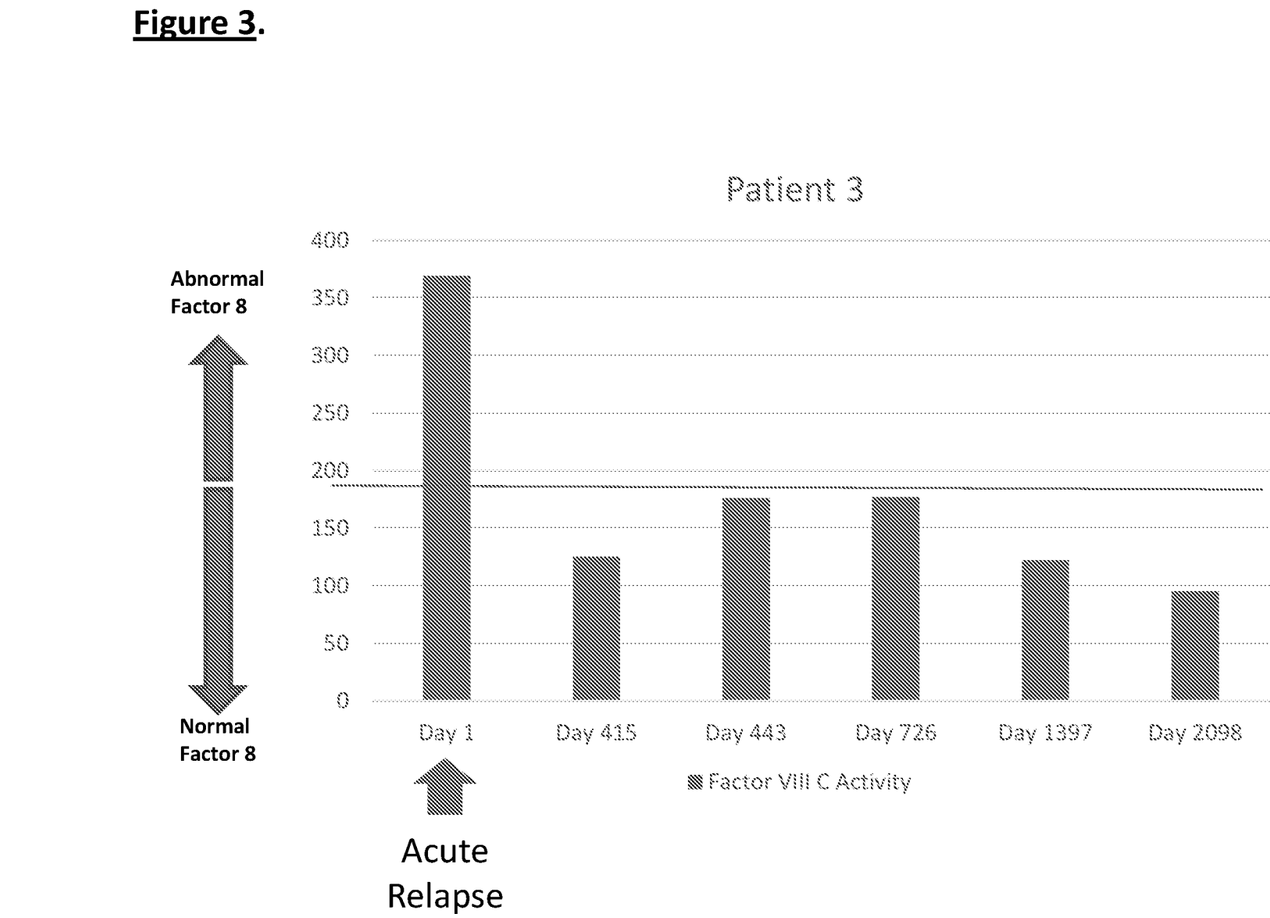
FIG. 3 depicts, in accordance with embodiments herein, acute refractory presenting relapse with diagnosis of leg weakness and sensory loss that never fully resolved despite prolonged steroid treatment. The subject is aged in her 50s and is a woman on various disease-modifying therapies.
Figure 4:
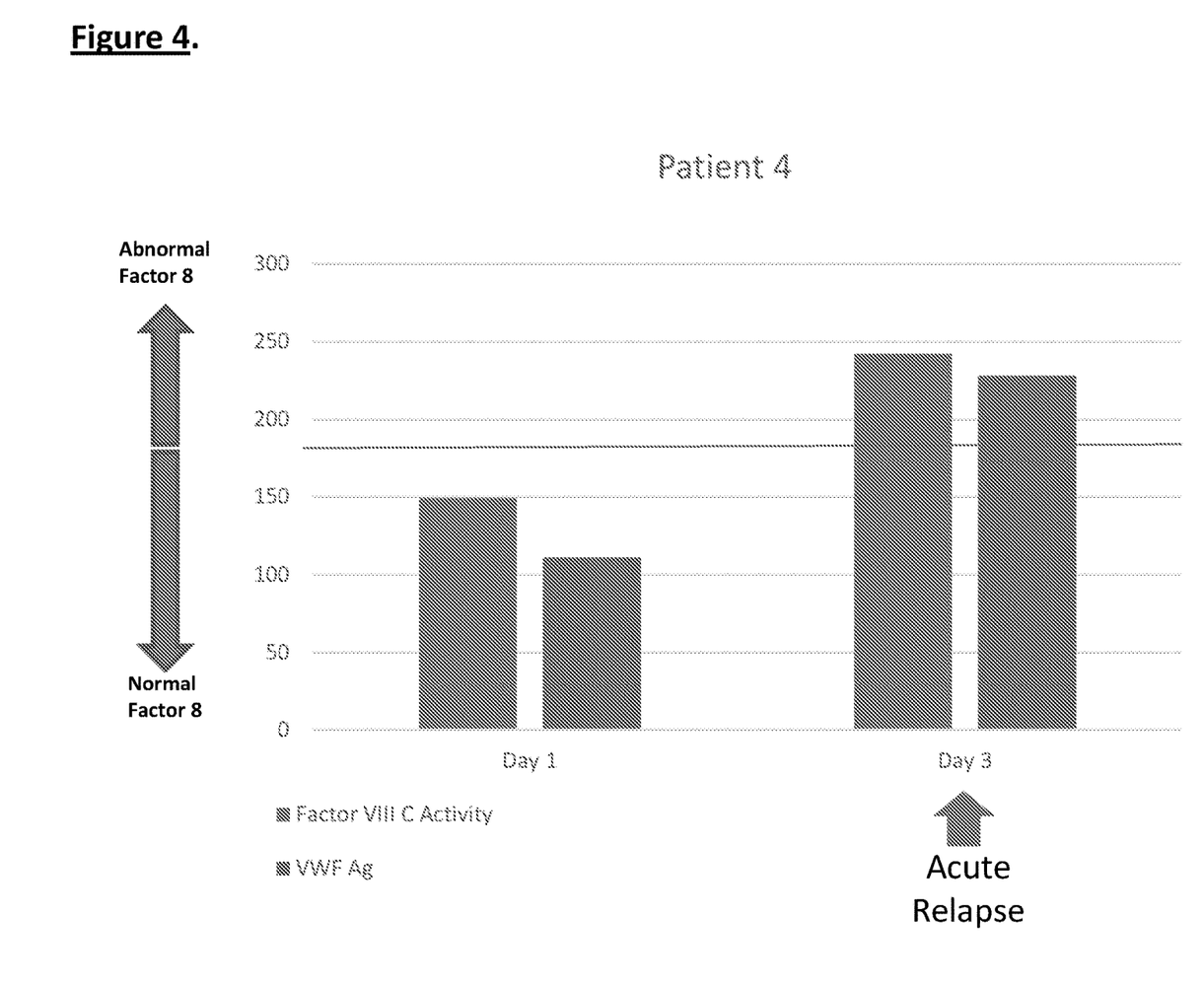
FIG. 4 depicts, in accordance with embodiments herein, acute relapse with increased leg weakness and little improvement. The subject is aged in his 50s, and is a man with established diagnosis on no disease-modifying therapy and new enhancing thoracic cord lesion.
Figure 5:
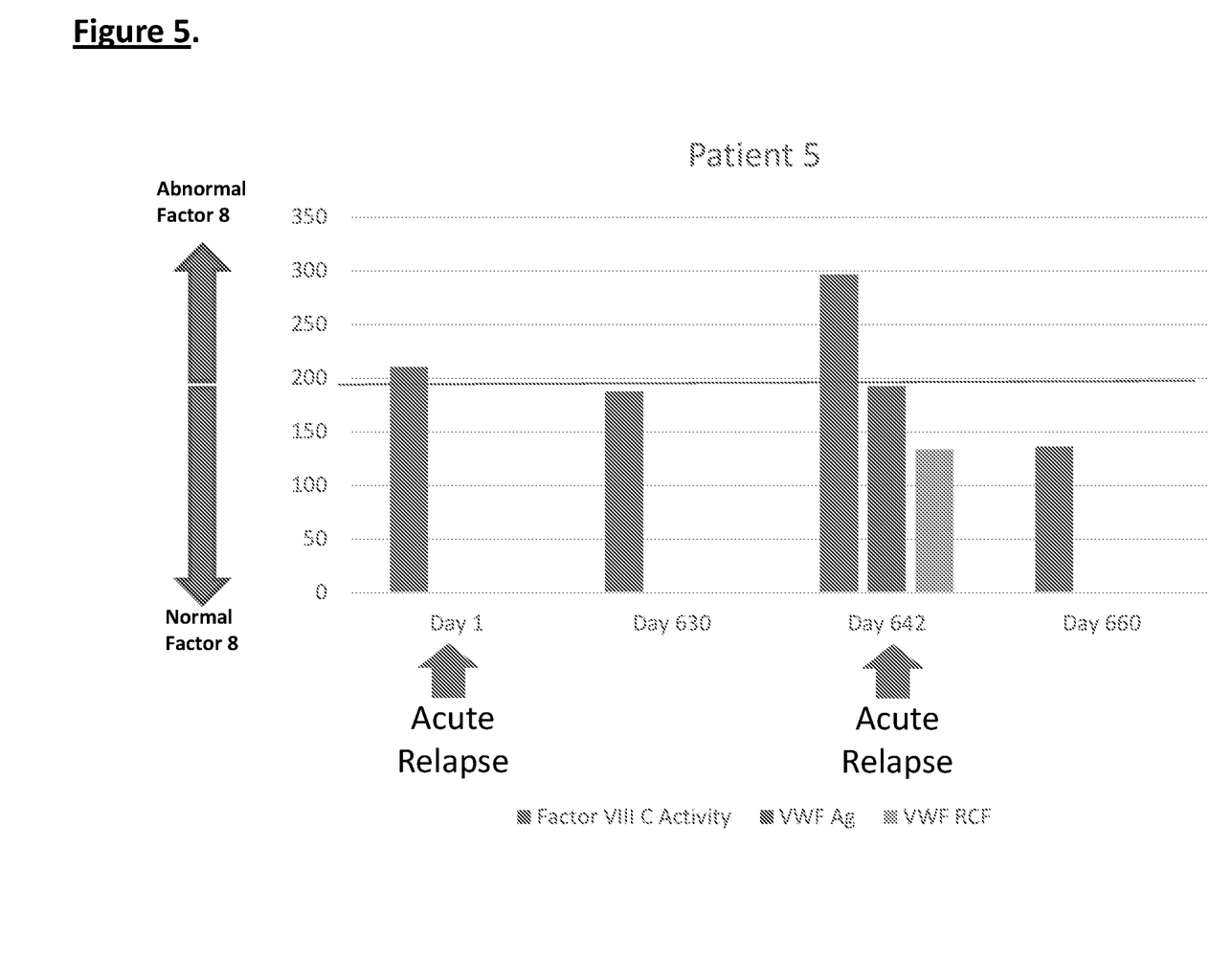
FIG. 5 depicts, in accordance with embodiments herein, acute relapse with vertigo and leg weakness on presentation and diagnosis. The subject is aged in his 60s, and is a male on TYSABRI® with relapse involving leg weakness. Specifically, the subject was on no disease modification therapy at diagnosis with vertigo, and was on TYSABRI® with a later relapse.
Figure 6:
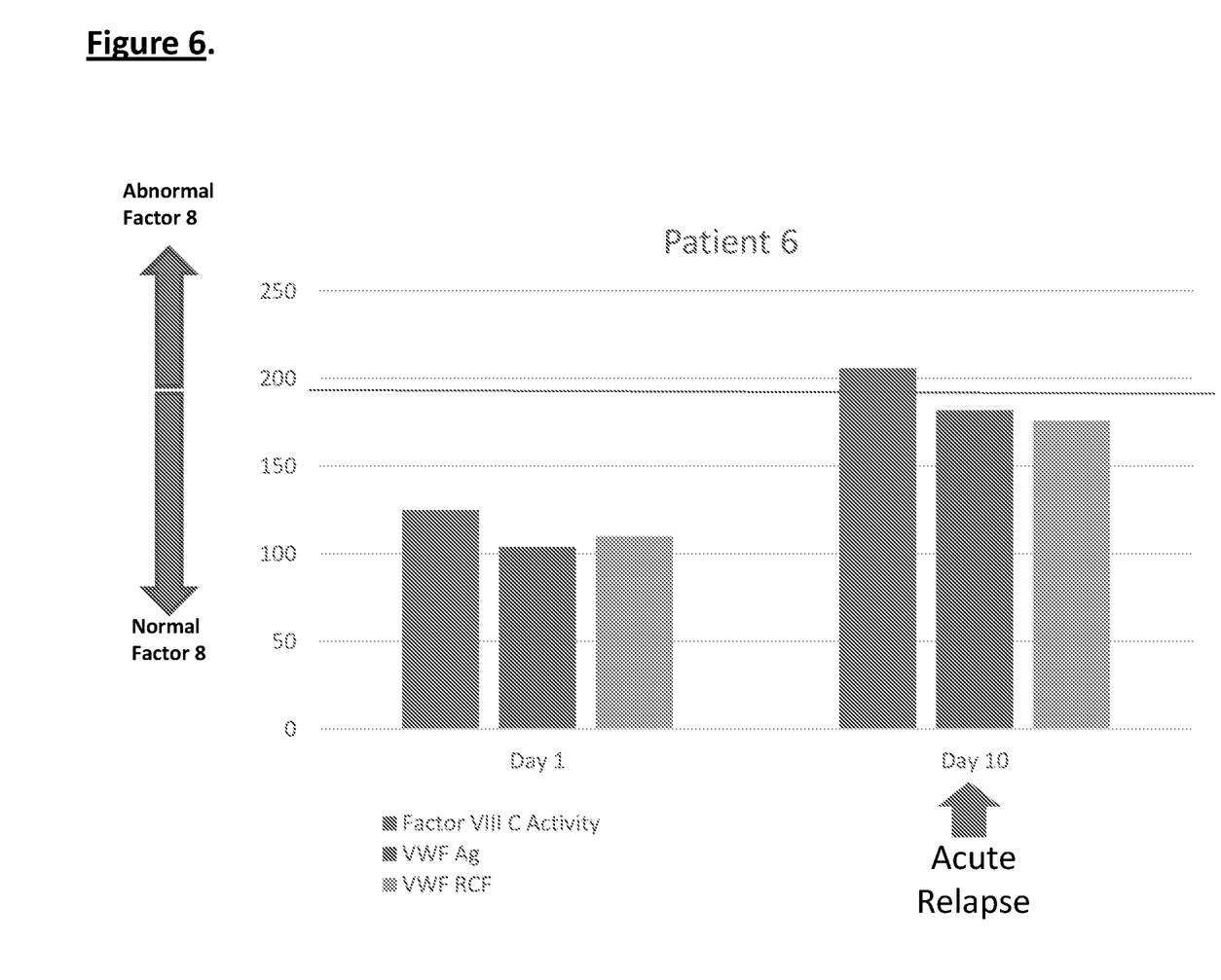
FIG. 6 depicts, in accordance with embodiments herein, acute relapse with blurry vision and near hemiplegia. The subject is aged in her 30s, and is a woman on COPAXONE®.
Figure 7:
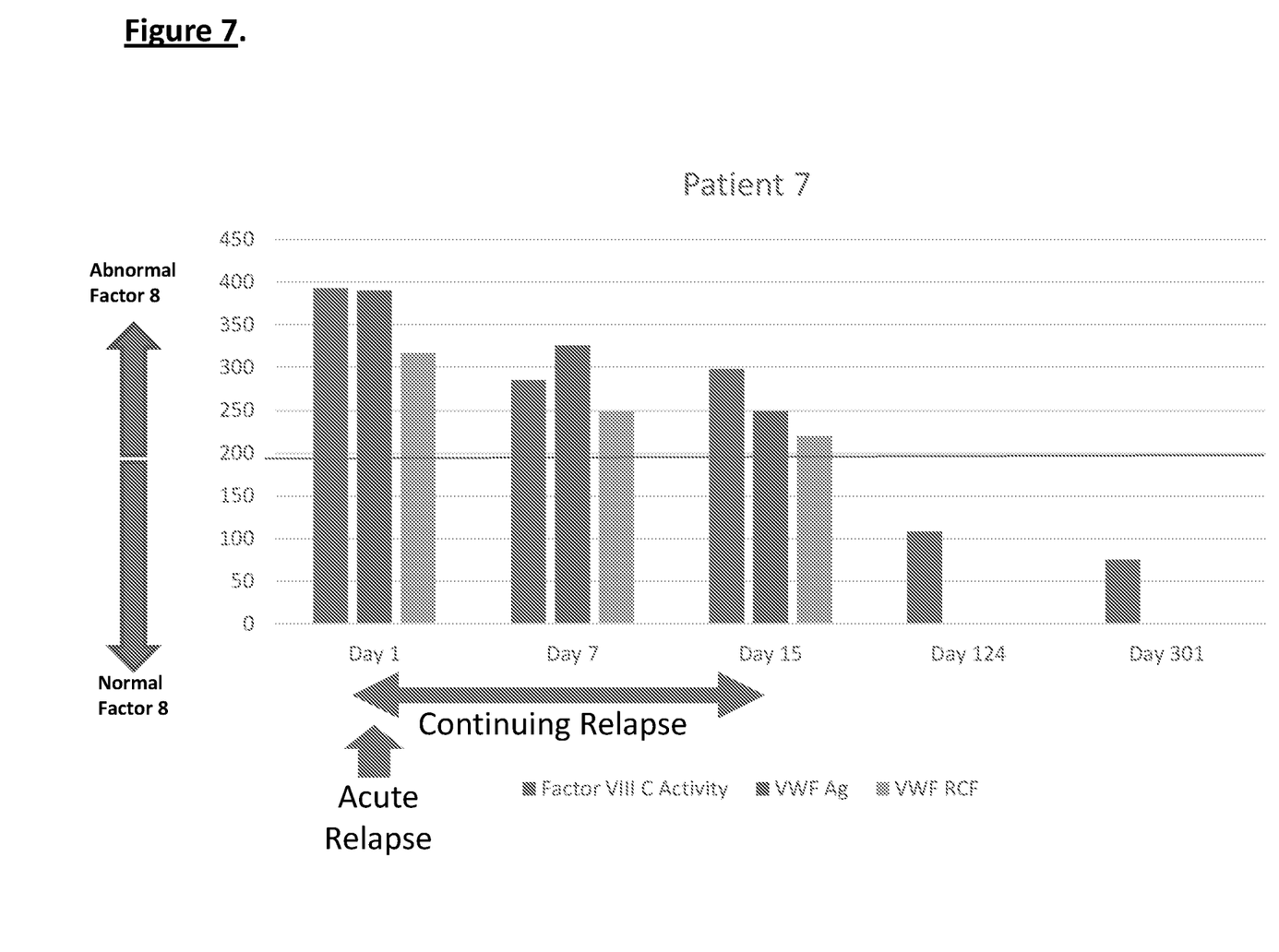
FIG. 7 depicts, in accordance with embodiments herein, acute relapse with inability to sit up. The subject is aged in her 50s, and is a woman on interferon therapy. Improvement with sustained, intermittent high dose steroid and physical therapy back to prior baseline. Factor VIII activity and von Willebrand Factor (vWF) antigen normalization found coincident with neurological improvement; high dose steroid treatment was used for a much longer regimen than standard treating algorithms suggest.
Figure 8:
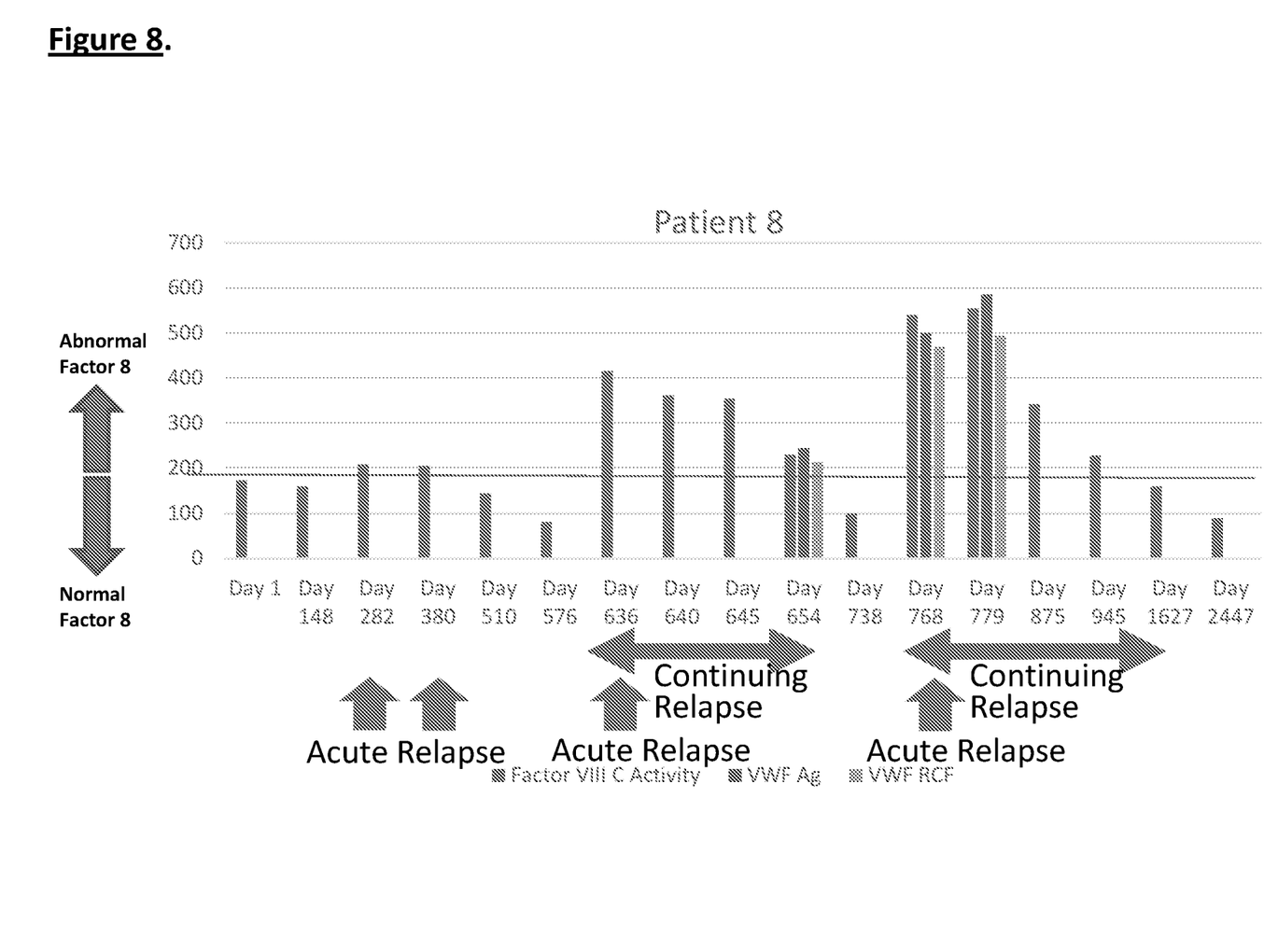
FIG. 8 depicts, in accordance with embodiments herein, acute severe relapses for a subject aged in her 60s. The subject is a woman with an established MS diagnosis, on different therapies including interferon therapy, to GILENYA®, RITUXAN® during a series of severe acute relapses. The patient responded to prolonged high dose steroids, as reflected by Factor VIII and vWF normalization during relapses and clinical improvement. However, without sustained steroids and further hospitalizations, could not maintain this improvement, and expanded disability status scale (EDSS) progressed from 6 on day 1 to EDSS 9 at day 2447.
Figure 9:
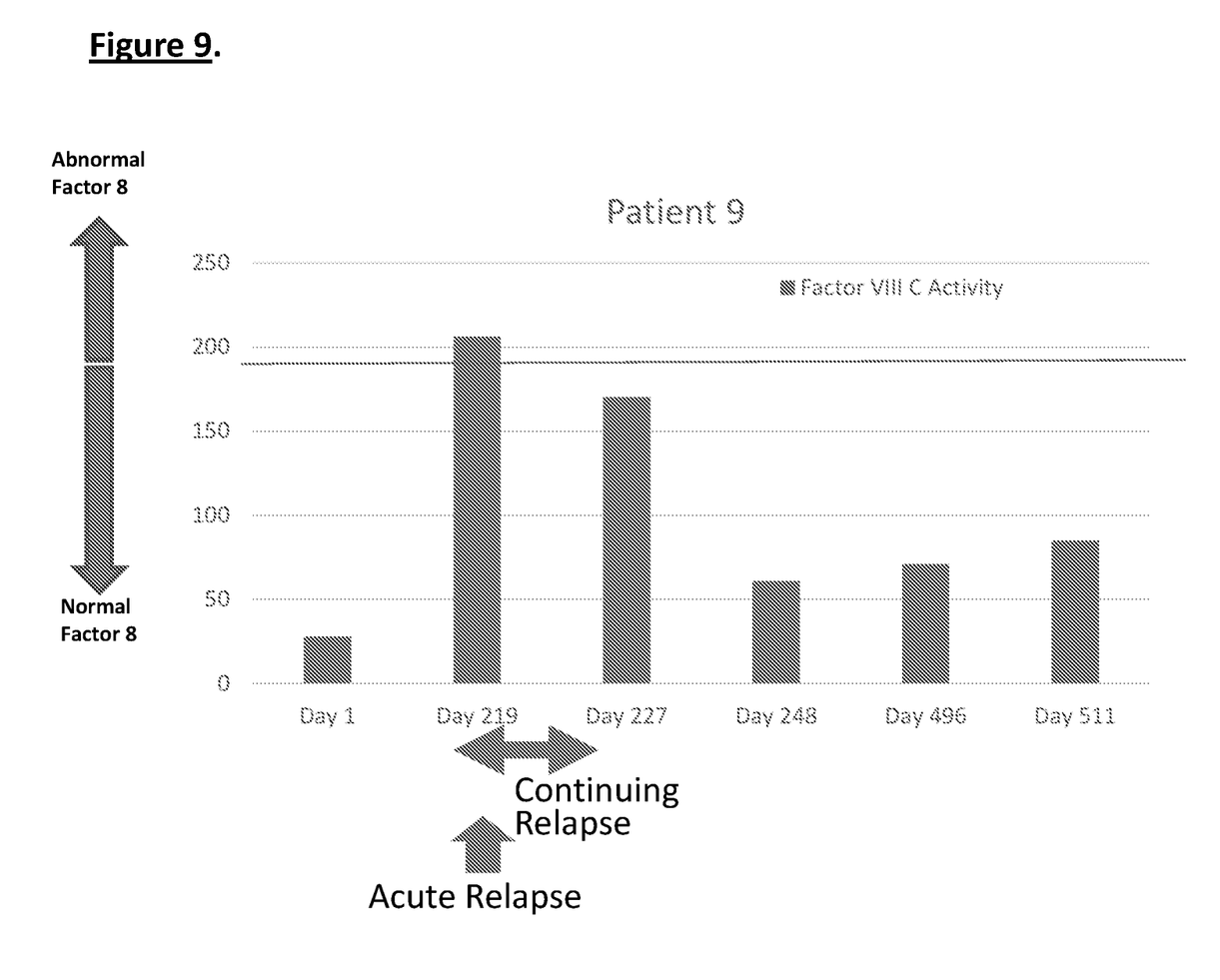
FIG. 9 depicts, in accordance with embodiments herein, acute relapse for a subject in her 40s. The subject is a woman on interferon therapy with an inability to stand. She clinically improved with prolonged steroid and physical therapy, as reflected by Factor VIII Activity and VWF antigen normalization, as well as therapy shift to Gilenya and pulse steroids.
Figure 10:
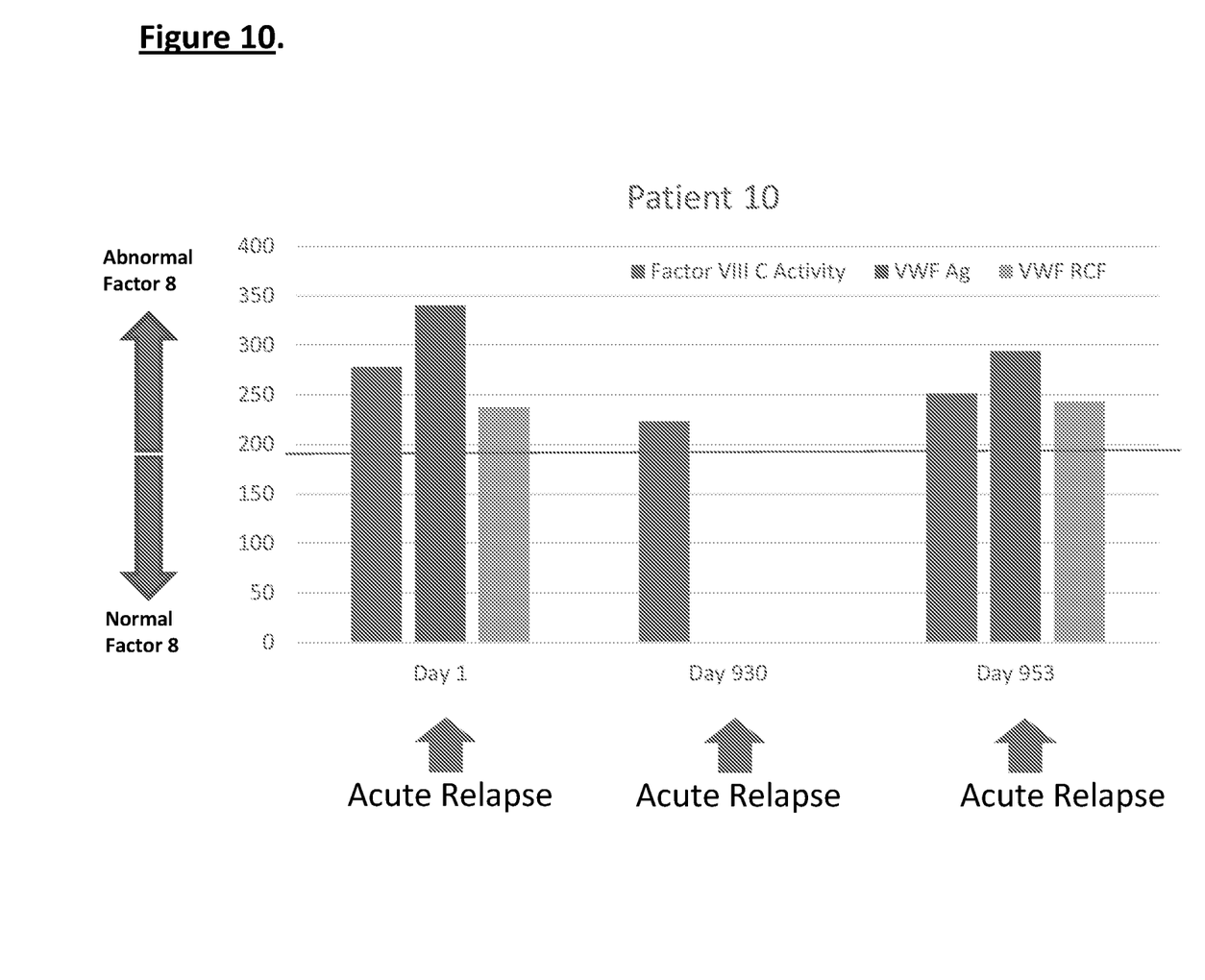
FIG. 10 depicts, in accordance with embodiments herein, acute relapse and near hemiplegia with enhancing thoracic cord lesion for a subject aged in her 40s. The subject is a woman on TYSABRI® with long, incomplete recovery process. Subsequent relapses were less severe with vertigo and gait imbalance. EDSS progression from 5.5 to 9 around first acute relapse, gradual improvement to 6.5, with worsening to 7.5 during subsequent relapses.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

Unless otherwise defined, all technical and scientific terms used herein have the same meaning as commonly understood by one of ordinary skill in the art to which this invention belongs.

Unless otherwise stated, the following terms used in this application, including the specification and claims, have definitions given below.

As used herein, the term "multiple sclerosis" or "MS" refers to an autoimmune disease affecting the central nervous system. MS is a disease of unknown etiology with a prolonged course involving many remissions and relapses. In some embodiments, individuals with multiple sclerosis experience a wide range of symptoms, including, but not limited to, double vision, blindness in one eye, muscle weakness, trouble with sensation, or trouble with coordination. Several forms of multiple sclerosis are known, and the terms "multiple sclerosis" or "MS", as used herein, is meant to include all such forms. Some commonly known forms of MS are benign multiple sclerosis (benign MS), relapsing-remitting multiple sclerosis (RRMS), secondary progressive multiple sclerosis (SPMS), primary progressive multiple sclerosis (PPMS), and progressive-relapsing multiple sclerosis (PRMS). In the relapsing forms of MS, such as, but not limited to, relapsing-remitting multiple sclerosis and progressive-relapsing multiple sclerosis symptoms may occur in isolated attacks known as relapses, attacks, crisis, exacerbation, or flare.

In accordance with various embodiments herein, the term "baseline," or "value of a baseline" is used. As used herein, the terms refer to a control value that could be particular to the specific individual under examination or treatment of a disease, such that it could be established, for example, by a physician examining blood values of a patient when a patient appears to be in remission or have few symptoms of disease, and thus create a baseline or value of a baseline for that patient or individual that can later serve as a future control value for that same patient or individual.

The terms "relapse," "attack," "crisis," "exacerbation," or "flare" as used herein refers to an increase in the severity of a disease or any of its signs or symptoms. In some embodiments the relapses last at least 24 hours. In some embodiments, the relapses may be associated with inflammation or demyelination in the brain or spinal cord. In some embodiments, the exacerbations last from a few days to several weeks, or several months. In some embodiments, the relapses are separated from the previous relapse by a period ranging from few days, or few weeks, or few months.

The term "treatment period" refers to the length of the time period wherein an individual is undergoing treatment for a disease. Similarly, the term "monitoring period" refers to the length of time wherein the progress of a disease or recovery from a disease in an individual is being monitored. During the treatment period or monitoring period, the individual may be under constant supervision of medical personnel or intermittent supervision.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

In various embodiments, the pharmaceutical compositions according to the invention, including anti-coagulation compounds and/or steroids for example, may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly.

As described herein, in accordance with various embodiments herein, the inventor has invented a technology for the diagnosing or predicting relapses in an individual afflicted with a form of multiple sclerosis. As further disclosed herein, clinical observations support that a disproportionate number of Multiple Sclerosis patients suffering refractory relapses will have transient abnormally elevated Factor VIII activity levels and elevated vWF Antigen levels in their blood during the onset and evolution of their relapse. Additionally, individualized high dose and persistent treatment with steroids tends to improve clinical function coincident with the normalization of abnormally elevated Factor VIII activity and vWF antigen levels.

In another embodiment, high levels of vwF Antigen levels, vWF Activity levels, and/or Factor VIII activity drive the severity of the MS relapse and can be measured peripherally, and that therapeutic strategies that lower these values improve clinical outcomes.

In various embodiments, disclosed herein is a method of detecting or predicting a relapse of multiple sclerosis in an individual afflicted with a form of multiple sclerosis, comprising: (a) providing a blood sample of the individual; (b) testing the blood sample to determine a protein activity or protein level, wherein the protein is Factor VIII, von Willebrand factor, or Protein C; and (c) detecting a relapse of multiple sclerosis in the individual if the protein activity or protein level is elevated compared to the protein activity or protein level in an individual not afflicted with the form of multiple sclerosis or the patient's own lowest baseline value as a form of a control. In some of these embodiments, the form of multiple sclerosis is relapsing-remitting multiple sclerosis with or without secondary progression. In some embodiments, the multiple sclerosis in the individual is in remission. In some embodiments, the blood sample test to determine the protein activity or protein level is performed simultaneously with other blood tests, such as, partial thromboplastin time (PTT) test, International Normalized Ratio (INR) test, and erythrocyte sedimentation rate (ESR) test. In some of these embodiments, the blood sample tests are performed at least once per month during the treatment period and/or monitoring period of multiple sclerosis. In some embodiments, an elevated Factor VIII activity indicates increased weakness and/or sensory impairment. In some embodiments, the individual may have an elevated Factor VIII activity or level when the Factor VIII level is equal to or more than 150, or when elevated more than 2 times the individual's baseline values. In some embodiments, the individual may have an elevated Factor VIII activity or level when the Factor VIII level is equal to or more than 160, or when elevated more than 2 times the individual's baseline values. In some embodiments, the individual may have an elevated Factor VIII activity or level when the Factor VIII level is equal to or more than 180, or when elevated more than 2 times the individual's baseline values. In other embodiments, the individual may have an elevated Factor VIII activity or level when the Factor VIII level is equal to or more than 191, or when elevated more than 2 times the individual's baseline values. In other embodiments, the individual may have an elevated Factor VIII activity or level when the Factor VIII level is more than 200, or when elevated more than 2 times the individual's baseline values. In some embodiments, the individual may have an elevated von Willebrand Factor activity when the von Willebrand Factor activity is more than 215, or when elevated more than 2 times the individual's baseline values. In some embodiments, the individual may have an elevated von Willebrand Factor level when the von Willebrand Factor level is more than 214, or when elevated more than 2 times the individual's baseline values. In some embodiments, the method of detecting or predicting a relapse of multiple sclerosis is used for patients who are at risk for more severe relapses. In some embodiments, the method is used for patients who are at risk of disability resulting from the relapse of multiple sclerosis.

In another embodiment, in accordance with various embodiments herein, Factor VIII activity and/or von Willebrand Factor antigen levels are checked daily. In another embodiment, Factor VIII activity and/or von Willebrand Factor antigen levels are checked weekly. Factor VIII activity and/or von Willebrand Factor antigen levels are checked monthly. Factor VIII activity and/or von Willebrand Factor antigen levels are checked at random intervals.

In various embodiments, disclosed herein is a method of treating an individual afflicted with multiple sclerosis, who is experiencing a relapse or predicted to experience a relapse, comprising: (a) detecting or predicting a relapse of multiple sclerosis in the individual as described herein; and (b) treating the individual by administering a dose of a steroid compound effective to alleviate the symptom of multiple sclerosis.

In another embodiment, the present invention provides a method of treating multiple sclerosis and/or relapsing multiple sclerosis with secondary progression by detecting a relapse of multiple sclerosis and administering a therapeutically effective dosage of solumedrol.

In various embodiments, disclosed herein is a method for an in-home and/or an in-hospital diagnosis of a relapse of multiple sclerosis in an individual, afflicted with a form of multiple sclerosis, comprising: (a) providing a testing kit for Factor VIII protein activity or level; (b) providing a blood sample of the patient; (c) testing the Factor VIII protein activity or level in the blood sample of the individual by using the testing kit; and (d) diagnosing a relapse of multiple sclerosis in the individual based on the elevated level or activity of Factor VIII protein compared to the activity or level of Factor VIII protein in an individual not afflicted with the form of multiple sclerosis. In some of these embodiments, the form of multiple sclerosis is relapsing-remitting multiple sclerosis. In some embodiments, the need for evaluation by a physician is determined based on the blood sample test result. In some embodiments, the need for evaluation by a physician is determined if the level or activity of Factor VIII protein is more than 150, or if greater than or equal to two times the patient's typical baseline values. In some embodiments, the recovery from a relapse of multiple sclerosis is determined based on the blood sample test result.

In various embodiments, disclosed herein is a method of determining the responsiveness to medicine of a patient undergoing a relapse of multiple sclerosis, comprising: (a) providing a blood sample of the patient; (b) testing the blood sample to determine the activity or level of a protein, wherein the protein is Factor VIII, von Willebrand factor, and/or Protein C; and (c) determining that the patient is responsive to medicine if the protein activity or protein level is not elevated or diminished compared to the protein activity or protein level in an individual not afflicted with multiple sclerosis. In one of these embodiments, the patient may have been previously tested as having an elevated level or activity of one or more of the proteins: Factor VIII, von Willebrand factor, and/or Protein C.

In various embodiments, disclosed herein is a method of determining the effectiveness of a therapy for multiple sclerosis, comprising: (a) providing a blood sample of an individual undergoing the therapy; (b) testing the blood sample to determine the activity or level of a protein, wherein the protein is Factor VIII, von Willebrand factor, and/or Protein C; and (c) determining that the therapy is effective if the protein activity or protein level is diminished compared to the protein activity or protein level of the individual before the therapy was started. In some of these embodiments, if the therapy is determined to be not effective, a modified therapy or treatment may be provided to the individual.

In various embodiments, disclosed herein is a method for selecting subjects for a clinical trial or study, comprising: (a) detecting a relapse of multiple sclerosis in a group of subjects using the method described herein; and (b) selecting those subjects for the clinical trial or study whose blood sample test shows an increased activity or level of a protein, wherein the protein is Factor VIII, von Willebrand factor, and/or Protein C.

Various embodiments include a method of treating multiple sclerosis, comprising co-administering to a patient in need of such treatment an effective amount of (i) an anti-coagulation compound, and (ii) a steroid. Some of these embodiments may further include a disease modifying agent. In some of these embodiments, the anti-coagulation compound may be Enoxaparin (e.g., LOVENOX®), Rivaroxaban (e.g., XARELTO®), Dabigatran (e.g., PRADAXA®), or Apixaban (e.g., ELIQUIS®). In some embodiments, the steroid may be a corticosteroid. In one embodiment, the corticosteroid may be dexamethasone, prednisone, methyl-prednisolone, or corticotropin (e.g., ACTHAR®). In another embodiment, the steroid is solumedrol. In one embodiment, the method described herein may be used to cross compare efficacies of improved disease modifying agents. In another embodiment, the present invention provides a method of treating multiple sclerosis, comprising administering to a patient in need of such treatment an effective amount of heparin derivatives, including but in no way limited to, Lovenox, Enoxaperin, and heparin.

Other embodiments include a method of reducing the number or severity of relapse in multiple sclerosis, comprising co-administering to a patient in need of such treatment an effective amount of (i) an anti-coagulation compound, and (ii) a steroid. In some of these embodiments, the anti-coagulation compound may be Enoxaparin (e.g., LOVENOX), Rivaroxaban (e.g., XARELTO®), Dabigatran (e.g., PRADAXA®), or Apixaban (e.g., ELIQUIS®). In some embodiments, the steroid may be a corticosteroid. In another embodiment, the steroid is solumedrol. In one embodiment, the corticosteroid may be dexamethasone, prednisone, methyl-prednisolone, or corticotropin (e.g., ACTHAR®).

In another embodiment, the patient is in need of treatment with an elevated Factor VIII activity, with Factor VIII activity considered elevated in an individual when it is elevated more than 2 times the individual's baseline values.

In one embodiment, Factor VIII activity is considered normal when it is between 56 and 160, or between 56 and 191, or between 56 and 200. In some embodiments, an elevated level of Factor VIII activity might serve as a warning for MS. In some embodiments, the patient may benefit from one or more doses of dexamethasone.

In one embodiment, von Willebrand Factor activity (also known as, Ristocetin Cofactor or RCF) is considered normal when it is between 51 and 215. An elevation in this number, say above 215, may serve as a warning for MS. In some embodiments, the patient might benefit from one or more doses of dexamethasone.

In one embodiment, von Willebrand Factor level (antigen) is considered normal when it is between 52 and 214. Factor VIII activity is elevated if it is above 214. In some embodiments, this might serve as a warning for MS. In some embodiments, the patient might benefit from one or more doses of dexamethasone.

In various embodiments, dexamethasone doses were administered to patients intravenously (IV) or orally. In another embodiment, IV solumedrol is administered to patients at between 500 mg to 1000 mg a day, for between 5 to 10 days, or intermittently. In another embodiment, doses are administered following labs and clinical examination. In one embodiment, IV doses of dexamethasone range from 50 mg to 100 mg per day for 3-5 days. In another embodiment, after that laboratory tests for Factor VIII and Von Willebrand Factor are repeated. If the results show elevated levels of these proteins and the patient is still weak, the treatment with dexamethasone is repeated. If the patient is feeling better, but test results still show elevated levels, then the dosage of dexamethasone is lowered or they are spaced out further until the test results normalize and the patient is clearly improved. In some embodiments, these "low dose" dexamethasone pulse treatments are administered to the patient weekly or monthly, until the patient returns to a stable state and does not have MS symptoms. In some embodiments, a large dose of dexamethasone may be administered to the patient if the patient is hospitalized and having a severe form of exacerbation. In one embodiment, a high dose of dexamethasone refers to 4 mg of dexamethasone administered intravenously every 6 hours for one or more days.

In one embodiment, patients suffering from a refractory relapse or had elevated Factor VIII or Von Willebrand Factor activity were treated with dexamethasone. In one embodiment, these patients improved within a few weeks or months of the treatment.

The present invention is also directed to a kit for determining Factor VIII, VWf antigen and/or Protein C activity or level. The kit is useful for practicing the inventive method of the diagnosis of a relapse of multiple sclerosis in an individual. The kit is an assemblage of materials or components, including at least one of the inventive compositions. Thus, in some embodiments the kit contains a composition including measurement of Factor VIII, VWf antigen and/or Protein C activity or level, as described above.

The exact nature of the components configured in the inventive kit depends on its intended purpose. For example, some embodiments are configured for the purpose of treating multiple sclerosis. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to diagnose a relapse of multiple sclerosis in an individual. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment.

The packaging materials employed in the kit are those customarily utilized in the medical field. As used herein, the term "package" refers to a suitable solid matrix or material such as glass, plastic, paper, foil, and the like, capable of holding the individual kit components. Thus, for example, a package can be a glass vial used to contain suitable quantities of an inventive composition for the diagnosis of a relapse of multiple sclerosis. The packaging material generally has an external label which indicates the contents and/or purpose of the kit and/or its components.

Embodiments of the present disclosure are further described in the following examples. The examples are merely illustrative and do not in any way limit the scope of the invention as claimed.

EXAMPLES

Example 1

Factor VIII Activity

Factor VIII is expressed at the blood brain barrier. It is a marker for brain endothelial cells and for the integrity of the blood brain barrier. Previous studies have shown that thrombin is activated in multiple sclerosis plaques and that thrombin inhibition may be useful for multiple sclerosis exacerbation recovery in animal models. Cellular signaling, direct fibrin deposition effects, and microglial effects have been implicated in this process as well. In one embodiment, disclosed herein is that elevated Factor VIII activity may signal a suitable subgroup of MS patients that could benefit from thrombin inhibition during recovery from a multiple sclerosis exacerbation.

In some embodiments, Factor VIII activity is not constantly high in an individual with high expanded disability status scale (EDSS). In one embodiment, there may be fluctuations that parallel a patient's disease course. A Factor VIII activity level greater than or equal to 160 has an approximate 99% correlation with multiple sclerosis exacerbation, showing symptoms such as acute sudden limb weakness, sensory loss, or gradual sustained loss in strength, or visual loss. In some embodiments, elevated fluctuations of Factor VIII activity may signal a treatable period of a multiple sclerosis exacerbation.

It is noted that not all clinical exacerbations and all exacerbations detected through Magnetic Resonance Imaging (MRI) are associated with an increase in Factor VIII activity. However, in one embodiment, patients who have a more severe exacerbation is likely to have increases in Factor VIII activity that may last for months. In one embodiment, this is seen through symptoms such as gait problems, increased spasticity in limbs, or likely spinal cord fluctuations.

In one embodiment, elevated Factor VIII activity during an exacerbation returns to normal when treated with one or more doses of steroids. In another embodiment, random Factor VIII activity checks may correlate with how well the multiple sclerosis or multiple sclerosis treatment is doing.

Example 2

Correlation of Factor VIII Activity with Exacerbation

The inventor has established a correlation of increased Factor VIII activity over time with exacerbation of MS. In one embodiment, the present invention provides an increased activity to be associated with slow-to-recover relapses of Multiple Sclerosis. In one embodiment, increased activity is associated with spinal Multiple Sclerosis exacerbations. In another embodiment, a patient is diagnosed with an elevated Factor VIII activity, and upon treatment with TYSABRI® or steroids, Factor VIII activity is returned to normal.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of treating an individual, comprising:
   detecting and/or predicting a relapse of multiple sclerosis (MS) in the individual by detecting levels of Factor VIII over a period in the individual, wherein the individual has been diagnosed with MS; and
   treating the individual by administering a medication effective to alleviate MS symptoms.

2. The method of claim 1, further comprising administering a disease-modifying therapy and/or agent.

3. The method of claim 1, wherein the medication is Enoxaparin, Rivaroxaban, Dabigatran, or Apixaban.

4. The method of claim 1, wherein the medication is a corticosteroid.

5. The method of claim 1, wherein the medication is dexamethasone, prednisone, methyl-prednisolone, or corticotropin.

6. The method of claim 1, wherein the medication is rivaroxaban.

7. The method of claim 1, wherein the medication is a heparin derivative.

8. The method of claim 1, wherein the medication is Enoxaperin; or heparin.

9. The method of claim 1, comprising administering solumedrol.

10. The method of claim 9, wherein a therapeutically effective dosage of solumedrol is determined by correlating an upregulation of von Willebrand factor and Factor VIII activity in the individual with a higher dosage to be administered to achieve clinical improvement.

11. The method of claim 1, wherein the individual is clinically suspected of suffering a period of acute MS relapse.

12. The method of claim 1, wherein detecting levels are obtained by assaying samples taken from the individual at least once every seven days during the period of acute MS relapse.

* * * * *